United States Patent [19]

Dohogne

[11] 4,244,360
[45] Jan. 13, 1981

[54] ORTHOPEDIC FIXATION PIN HOLDER

[75] Inventor: Charles L. Dohogne, San Pedro, Calif.

[73] Assignee: Ace Orthopedic Manufacturing, Inc., Hawthorne, Calif.

[21] Appl. No.: 87,218

[22] Filed: Oct. 22, 1979

[51] Int. Cl.³ .............................................. A61F 5/04
[52] U.S. Cl. .................................................. 128/92 A
[58] Field of Search .............. 128/92 A, 92 B, 92 BA, 128/92 EB, 92 ED

[56] References Cited

U.S. PATENT DOCUMENTS

| 1,997,466 | 4/1935 | Longfellow | 128/92 A |
| 2,346,346 | 4/1944 | Anderson | 128/92 A |
| 2,391,537 | 12/1945 | Anderson | 128/92 A |
| 2,439,995 | 4/1948 | Thrailkill | 128/92 A |
| 2,536,963 | 1/1951 | Stephens | 128/92 EB |

Primary Examiner—Robert W. Michell
Assistant Examiner—C. W. Shedd
Attorney, Agent, or Firm—Knobbe, Martens, Olson, Hubbard & Bear

[57] ABSTRACT

An improved orthopedic fixation pin holder device is disclosed composed generally of a body member having a pin receiving aperture formed therethrough and a locking member slidingly mounted within the body member including a mating pin receiving aperture formed therethrough. Both apertures are provided with opposingly disposed V-shaped wall portions which apply a concentrated shearing force at discrete locations along the pin diameter to positively clamp the pin within the pin holder.

1 Claim, 3 Drawing Figures

U.S. Patent  Jan. 13, 1981  4,244,360
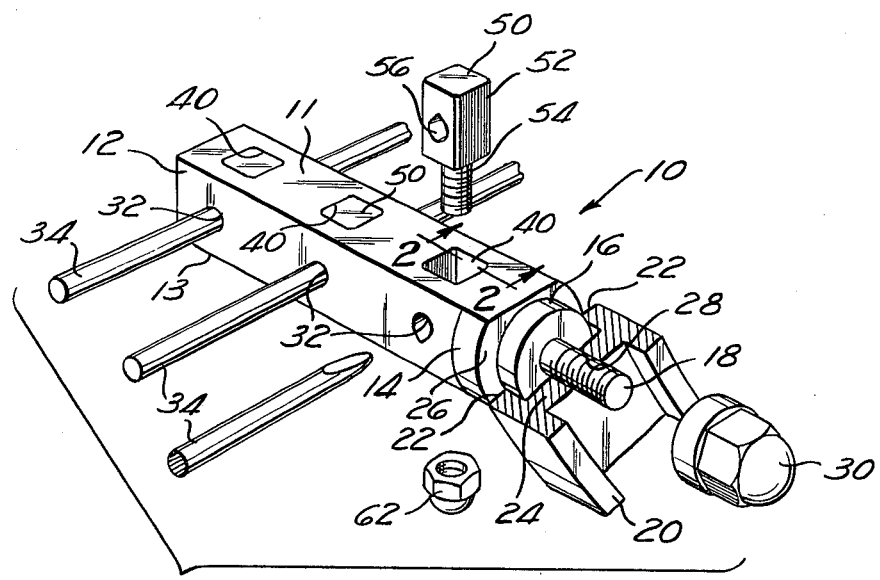
Fig.1
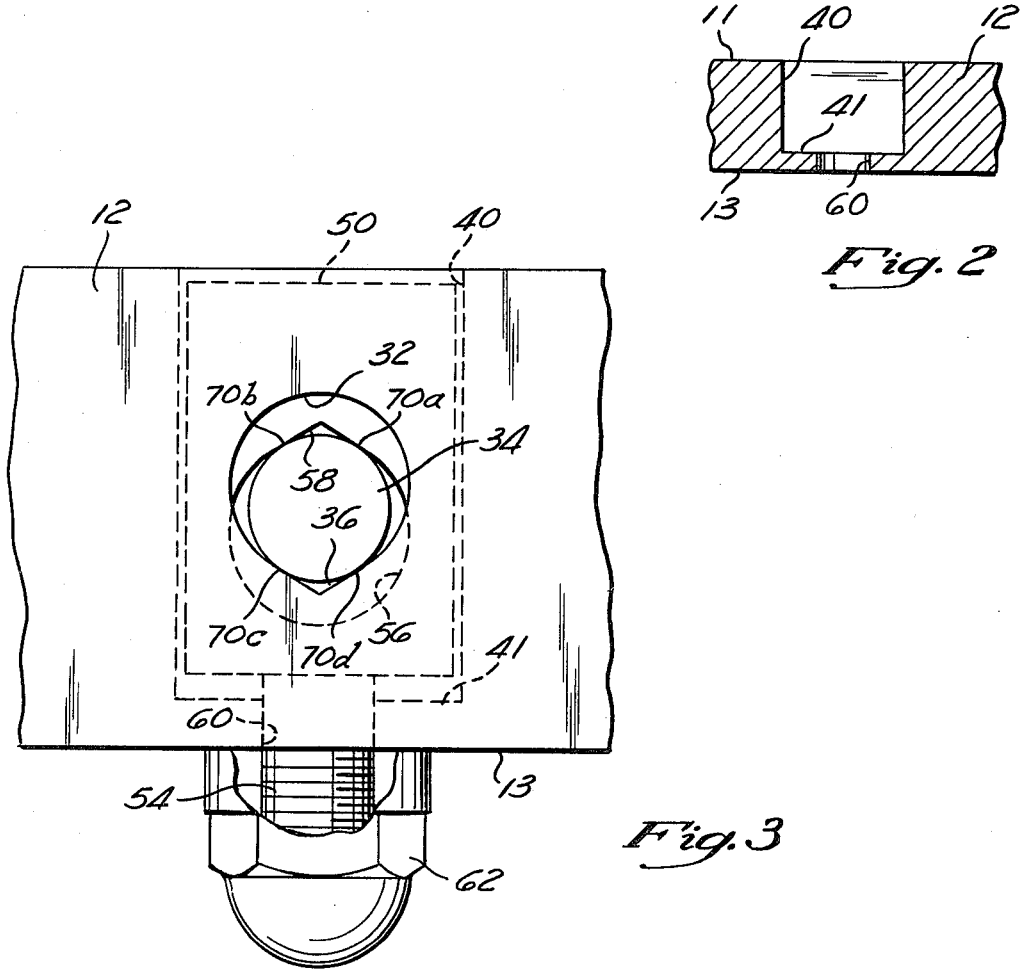
Fig.2
Fig.3

ORTHOPEDIC FIXATION PIN HOLDER

BACKGROUND OF THE INVENTION

The present invention relates to medical pin holder devices and more particularly to medical pin holder devices utilized in orthopedic external fixation apparatus wherein the repositioning and immobilization of a fractured bone is facilitated by means external of the soft tissue surrounding the fractured bone.

Various external fixation devices are currently available in the marketplace, all of which in one form or another utilize plural transfixing and/or half pins positioned on opposite sides of a bone fracture which extend through the fractured bone and outward beyond the soft tissue surrounding the bone. The exposed ends of the plural pins are rigidly attached to one or more pin holders which are interconnected by multiple adjustment rods to form an external frame about the soft tissue of a patient. By adjusting the relative orientation of the pin holders on opposite sides of the fracture and securely maintaining a desired orientation during rehabilitation, the bone fracture may be accurately realigned to permit proper healing of the fracture. Thus, the pin holders form an integral component of the entire orthopedic external fixation device which must be capable of rigidly clamping the pins in a desired position to provide complete immobilization of the bone fracture.

Heretofore, the prior art pin holder devices utilized in orthopedic external fixation apparatus have been formed in various design configurations, all of which have provided for the selective clamping of either singular or multiple pins within the pin holder. Although such prior art pin holder devices have proven useful in general applications, there are inherent deficiences associated in their use.

These inherent deficiencies have focused primarily upon the prior art pin holder's inability to provide sufficient clamping forces to positively prevent movement of the pins within the pin holder as well as a failure to provide any means for the independent removal or adjustment of individual pins upon the pin holder. As such, the prior art devices have often permitted to undesirable movement of the fractured bone during rehabilitation or limited operative and post-operative adjustment and modification of the pins upon the patient.

Thus, there exists a substantial need for an improved external fixation pin holder device which rigidly clamps the pin in a desired position, and additionally provides for the independent adjustment of multiple pins within the pin holder.

SUMMARY OF THE PRESENT INVENTION

The present invention comprises an improved external fixation pin holder device which significantly eliminates the deficiencies associated in the prior art. Specifically, the present invention comprises a pin holder device which positively clamps individual pins within the pin holder and facilitates the independent adjustment of a desired pin without disturbing the remaining pins within the pin holder.

The improved clamping and adjustment features of the present invention are made possible by a novel pin holder body and reciprocal pin lock member arrangement wherein individual pins extend through a pair of aligned apertures formed in the body member and pin lock member. Both of the apertures are provided with a V-shaped clamping section on opposed portions of their cylindrical walls, which are adapted to tangentially contact the diameter of the pin along discrete clamping lines. By manually reciprocating the pin lock member in a direction perpendicular to the axis of the aligned apertures, the V-shaped sections center the pin within the apertures, and apply a concentrated shearing force to the pin which positively clamps the pin within the pin holder.

Additionally, in the preferred embodiment, the present invention provides multiple pin lock members in the body portion of the device, each of which may be independently reciprocated within the body portion to permit selective adjustment of individual pins without disturbing the remaining pins within the pin holder.

DESCRIPTION OF THE DRAWINGS

These as well as other features of the present invention will become more apparent upon reference to the drawings wherein:

FIG. 1 is a partially exploded perspective view of the pin holder of the present invention, illustrating its detailed construction and depicting a manner in which it may be mounted to a support frame of the external fixation device;

FIG. 2 is a cross-sectional view of a portion of the pin holder of FIG. 1 taken about lines 2—2 of FIG. 1 showing the shape and orientation of a pocket formed therein which receives the pin lock member of FIG. 1; and FIG. 3 is an enlarged partial side view of the pin holder of FIG. 1, illustrating the manner in which an individual pin is rigidly locked in place within the pin holder.

DETAILED DESCRIPTION OF THE PREFERRED EMBODIMENT

Referring to FIG. 1, there is shown the improved pin holder device 10 of the present invention which is specifically adapted for use upon a particular orthopedic external fixation device developed by Dr. David Fischer, and assigned to Ace Orthopedic Manufacturing (the assignee of the subject application). A complete description of such an external fixation device is contained in the recently filed United States patent application by Dr. David Fischer, entitled IMPROVED EXTERNAL FIXATION DEVICE (Serial Number unknown), the disclosure of which is expressly incorporated herein by reference.

As shown in FIG. 1, the pin holder 10 of the present invention is formed having an elongate body section 12 including a flange 14 at its distal end. The flange 14 is provided with a mounting boss 16 and threaded stud 18 which are adapted to mount the pin holder 10 to an I-beam frame segment 20 of the external fixation device (not shown). The length of the mounting boss 16 is formed slightly less than the distance between the outboard edges 22 and web portion 24 of the frame segment 20, such that the lower surface 26 of the flange 14 may abut the outboard edges 22 of the frame segment 20. With the threaded stud 18 inserted through a mounting aperture 28 formed in the frame segment 20, an acorn fastener 30 may be threaded onto the stud 18, from the opposite side of the frame segment 12, thereby rigidly mounting the pin holder 10 to the frame segment.

By such an arrangement, the pin holder 10 may be selectively rotated about the axis of the threaded stud 18 and subsequently locked in a desired orientation by the manual tightening of the acorn fastener 30 against the web portion 24 of the frame segment 12. Further, it will be recognized that the mounting boss 16 and threaded stud 18 may be modified with other conventional mounting means to permit the pin holder 10 of the present invention to be utilized on other particular types of external fixation devices (not shown).

The body section 12 of the pin holder 10 includes a plurality of apertures 32 extending through its width, each sized to loosely receive the exposed end of a transfixing or half pin 34 which extends through the body's soft tissue (not shown) and into the fractured bone (not shown). As best shown in FIG. 3, the lower portion of each of the apertures 32 is formed with a V-shaped wall portion 36 having an included angle of approximately 120 degrees.

A plurality of rectangular pockets 40 are formed in the body section 12 of the pin holder 14 being disposed perpendicular to the apertures 32. The pockets 40 initiate at the upper surface 11 of the body section 12 terminating at a distance below the apertures 32 but above the lower surface 13 of the body section 12 (shown in FIG. 2). Pockets of any other non-circular shape may, of course, be used.

Each of the pockets 40 are sized to slidingly receive a pin lock member 50 having a rectangular shaped body 52 and a threaded stud 54. The body 52 of the pin lock member 50 includes a central aperture 56 which extends through the pin lock member 50 and is provided with a V-shaped wall portion 58 adjacent its upper end, which is formed in the manner previously described in relation to the V-shaped wall 36 of the apertures 32. The threaded stud 54 of the pin lock member 50 extends through an aperture 60 (see FIG. 2) formed centrally between the lower surface 41 of the pocket 40 and the bottom surface 13 of the body section 12, and receives an acorn fastener 62.

The operation of the pin holder 10 of the present invention may be described with specific reference to FIGS. 1 and 3. In operation, the pin lock member 50 is loosely positioned within one of the pockets 40 formed in the body section 12, and the exposed end of the transfixing or half pin 34 inserted through both of the apertures 32 and 56 formed in the body section 12 and pin lock member 50, respectively. Subsequently, the acorn fastener 62 may be mounted onto the threaded stud 54 causing the pin lock member 50 to be pulled tightly downward toward the lower surface 41 of the pocket 40.

During this downward movement of the pin lock member 50, the horizontal center line of the aperture 56 formed in the pin lock member 50 passes beneath the horizontal center line of the aperture 32 formed in the body section 12, whereby the opposed V-shaped wall portions 36 and 58 contact the outside diameter of the pin 34. Due to the V-shaped configuration of the wall portions 36 and 58, upon contact therewith, the pin 34 is self-centered along the aligned vertical center lines of the apertures 32 and 56.

Continued manual tightening of the acorn fastener 62 causes the pin 18 to be tightly clamped between the opposing V-shaped wall portions 36 and 58 with the clamping forces being concentrated along four discrete clamping lines 70a, 70b, 70c, and 70d corresponding to the tangential contact between the outer diameter of the pin 34 with the V-shaped wall portions 36 and 58. The application of the concentrated clamping forces along the four discrete clamping lines 70a through 70d generates a shearing force upon the pin 34 which has been found to positively clamp the pin 34 within the pin holder 14.

Additionally, as shown in FIG. 1, each of the pockets 40 formed in the body section 12 of the pin holder 14 is provided with a respective pin lock member 50 which facilitates multiple pins 34 to be positively clamped within the pin holder 10. Due to each of the pins 34 being mounted to the pin holder 10 by use of a separate pin lock member 50, individual pins may be selectively adjusted within the pin holder 10 by merely loosening the appropriate acorn fastener 62 from the respective pin lock member 50 without disturbing or affecting the other pins 34 in the holder 10. As such, the present invention permits an orthopedic surgeon to independently adjust and modify pin fixation upon the patient to meet necessary operative and post-operative procedures.

Thus, in summary, the pin holder 10 of the present invention, by use of the noval V-shaped wall portions 36 and 58 and individual pin lock members 50 yields independent positive clamping of multiple pins 34 upon an external fixation device. Although in the preferred embodiment the pin holder 14 is formed to clamp three individual pins 34, those skilled in the art will recognize the teachings of the present invention are equally applicable to single as well as multiple pin clamping operations. Also, while the description refers to certain orientation as upper and lower, it will be evident that this is only for convenience and description and does not limit the orientation of the present invention.

I claim:

1. In a pin holder for use on an orthopedic external fixation device comprising a body member adapted to be mounted to said external fixation device, a first aperture extending through said body member sized to receive a pin therein, a second aperture extending through said body member aligned with and oriented perpendicular to said first aperture, including an enlarged aperture portion initiating at one end of said second aperture and terminating at a distance spaced from the opposite end of said second aperture, and a locking member slidingly positioned within said enlarged aperture portion including a pin receiving aperture oriented parallel to said first aperture, said locking member including means for reciprocating said locking member within said enlarged aperture portion to cause said pin receiving aperture and said first aperture to tightly contact opposite sides of a pin inserted through said apertures, said improvement comprising:

a V-shaped recess formed on opposing wall portions of said pin receiving aperture and said first aperture, said recesses tangentially contacting said pin at discrete locations along the diameter of said pin to apply a shear force to said pin to positively clamp said pin in said pin holder.

* * * * *